US010168286B2

(12) United States Patent
Hirai et al.

(10) Patent No.: US 10,168,286 B2
(45) Date of Patent: Jan. 1, 2019

(54) DEFECT OBSERVATION DEVICE AND DEFECT OBSERVATION METHOD

(71) Applicant: Hitachi High-Technologies Corporation, Minato-ku, Tokyo (JP)

(72) Inventors: Takehiro Hirai, Tokyo (JP); Hideki Nakayama, Tokyo (JP); Kenichi Nishigata, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 37 days.

(21) Appl. No.: 15/533,424

(22) PCT Filed: Dec. 10, 2014

(86) PCT No.: PCT/JP2014/082609
§ 371 (c)(1),
(2) Date: Jun. 6, 2017

(87) PCT Pub. No.: WO2016/092640
PCT Pub. Date: Jun. 16, 2016

(65) Prior Publication Data
US 2018/0266968 A1 Sep. 20, 2018

(51) Int. Cl.
*H01J 37/26* (2006.01)
*H01J 37/28* (2006.01)
(Continued)

(52) U.S. Cl.
CPC ....... *G01N 21/956* (2013.01); *G01N 21/9501* (2013.01); *H01J 37/28* (2013.01); *H01L 22/12* (2013.01); *G01N 2223/6116* (2013.01)

(58) Field of Classification Search
CPC ............. G01N 21/956; G01N 21/9501; G01N 2223/6166; H01J 37/28; H01L 22/12
(Continued)

(56) References Cited

U.S. PATENT DOCUMENTS 7,095,507 B1 * 8/2006 Hwang .............. G01B 11/2441
356/511
7,728,294 B2 * 6/2010 Hiroi .................... G01R 31/307
250/306
(Continued)

FOREIGN PATENT DOCUMENTS

JP 2005-274172 A 10/2005
JP 2007-305760 A 11/2007
(Continued)

OTHER PUBLICATIONS

International Search Report (PCT/ISA/210) issued in PCT Application No. PCT/JP2014/082609 dated Mar. 10, 2015 with English translation (five pages).
(Continued)

*Primary Examiner* — Nicole Ippolito
(74) *Attorney, Agent, or Firm* — Crowell & Moring LLP

(57) ABSTRACT

In a scheme for analyzing low magnification defect images and determining whether or not a defect detection method using cell comparison is applicable, if a defect detection method using cell comparison cannot be applied and the proportion transitioning to a defect detection method using die comparison increases, throughput may decrease even more than starting out with defect detection by a defect detection method using die comparison. The purpose of present invention is to carry out high precision defect detection with a stable throughput. In the present invention, the defect detection processing mode applied for detecting defects from the defect image is determined using a reference image, and defects are detected from the defect image by the defect detection processing mode that has been determined.

20 Claims, 8 Drawing Sheets

(51) Int. Cl.
*G01N 5/00* (2006.01)
*G01N 21/956* (2006.01)
*G01N 21/95* (2006.01)
*H01L 21/66* (2006.01)

(58) Field of Classification Search
USPC .................. 250/306, 307, 309, 310, 311
See application file for complete search history.

(56) References Cited

U.S. PATENT DOCUMENTS

| | | | |
|---|---|---|---|
| 2001/0055415 A1* | 12/2001 | Nozaki | G01N 21/8851 |
| | | | 382/141 |
| 2005/0045821 A1* | 3/2005 | Noji | G01N 23/225 |
| | | | 250/311 |
| 2008/0067371 A1 | 3/2008 | Kurihara et al. | |
| 2009/0074286 A1* | 3/2009 | Kitazawa | G01N 21/9501 |
| | | | 382/144 |
| 2009/0222753 A1* | 9/2009 | Yamaguchi | G06T 7/0004 |
| | | | 715/771 |
| 2009/0268959 A1 | 10/2009 | Harada et al. | |
| 2011/0285839 A1 | 11/2011 | Kotaki et al. | |
| 2011/0320149 A1* | 12/2011 | Lee | G01N 21/9501 |
| | | | 702/83 |
| 2015/0279024 A1 | 10/2015 | Tsuchiya et al. | |

FOREIGN PATENT DOCUMENTS

| | | |
|---|---|---|
| JP | 2009-283917 A | 12/2009 |
| JP | 2010-161247 A | 7/2010 |
| JP | 2014-181966 A | 9/2014 |

OTHER PUBLICATIONS

Japanese-language Written Opinion (PCT/ISA/237) issued in PCT Application No. PCT/JP2014/082609 dated Mar. 10, 2015 (three pages).

* cited by examiner

[Fig. 1]
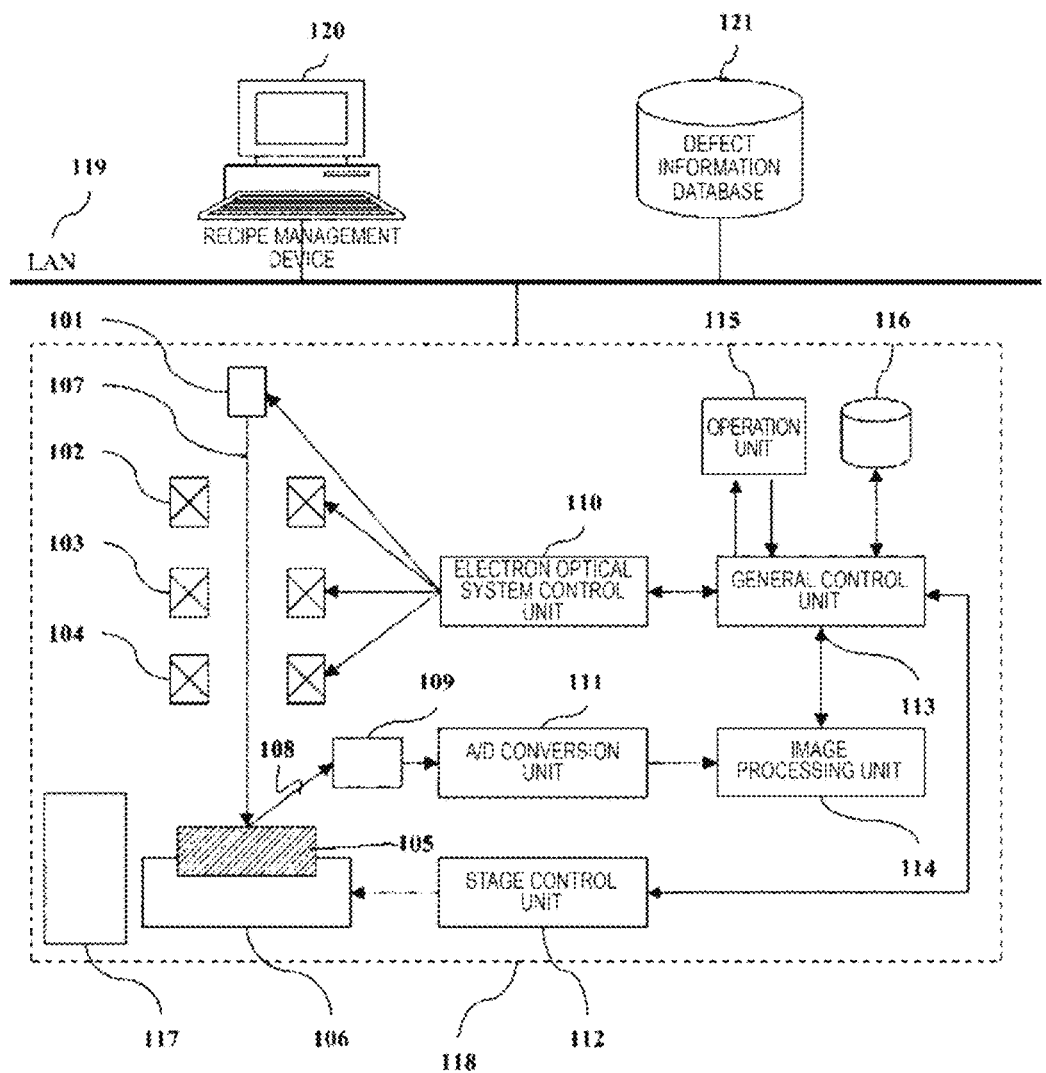

[Fig. 2]
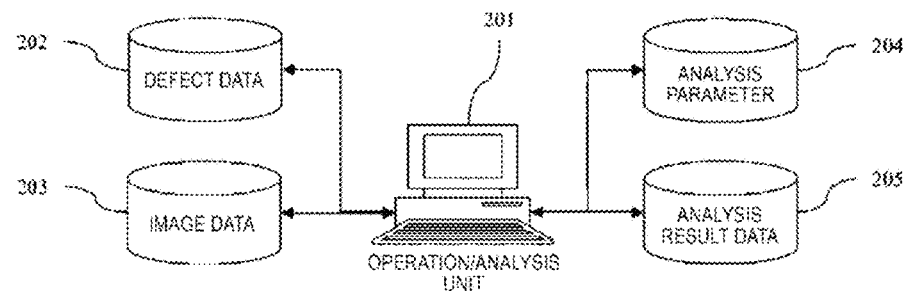
[Fig. 3]
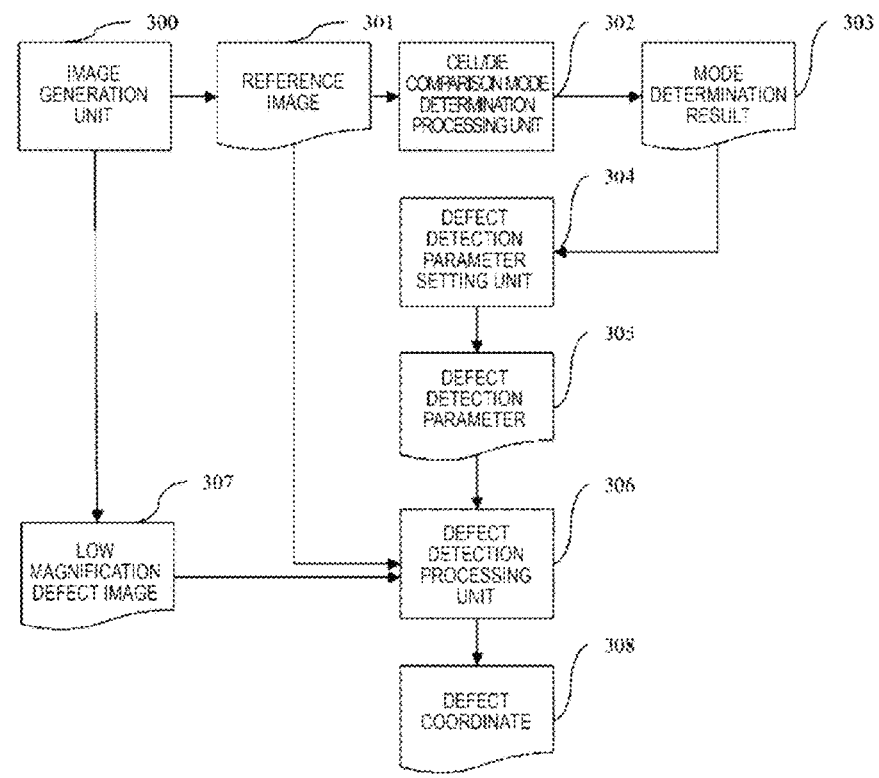

[Fig. 4]
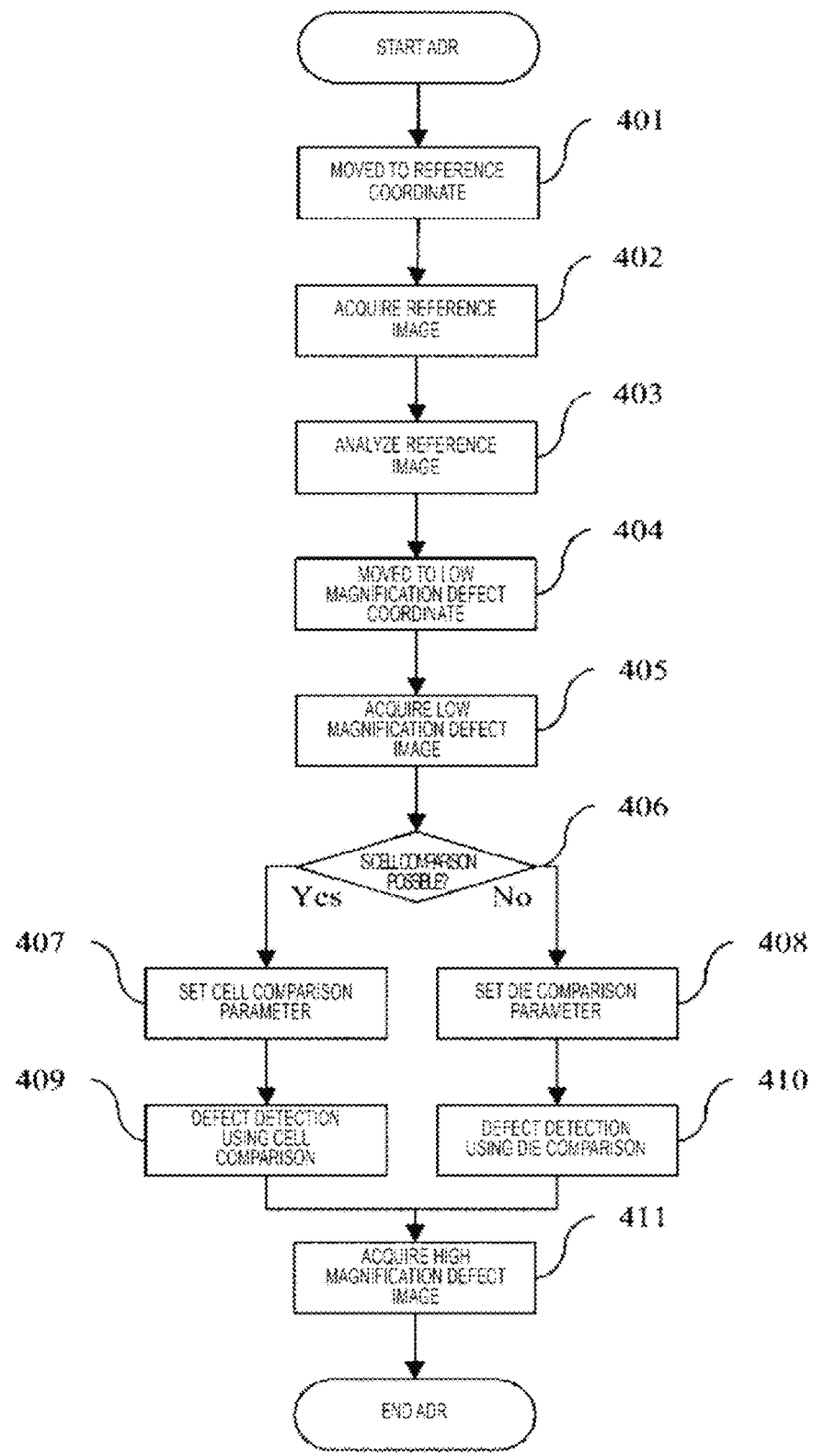

[Fig. 6]
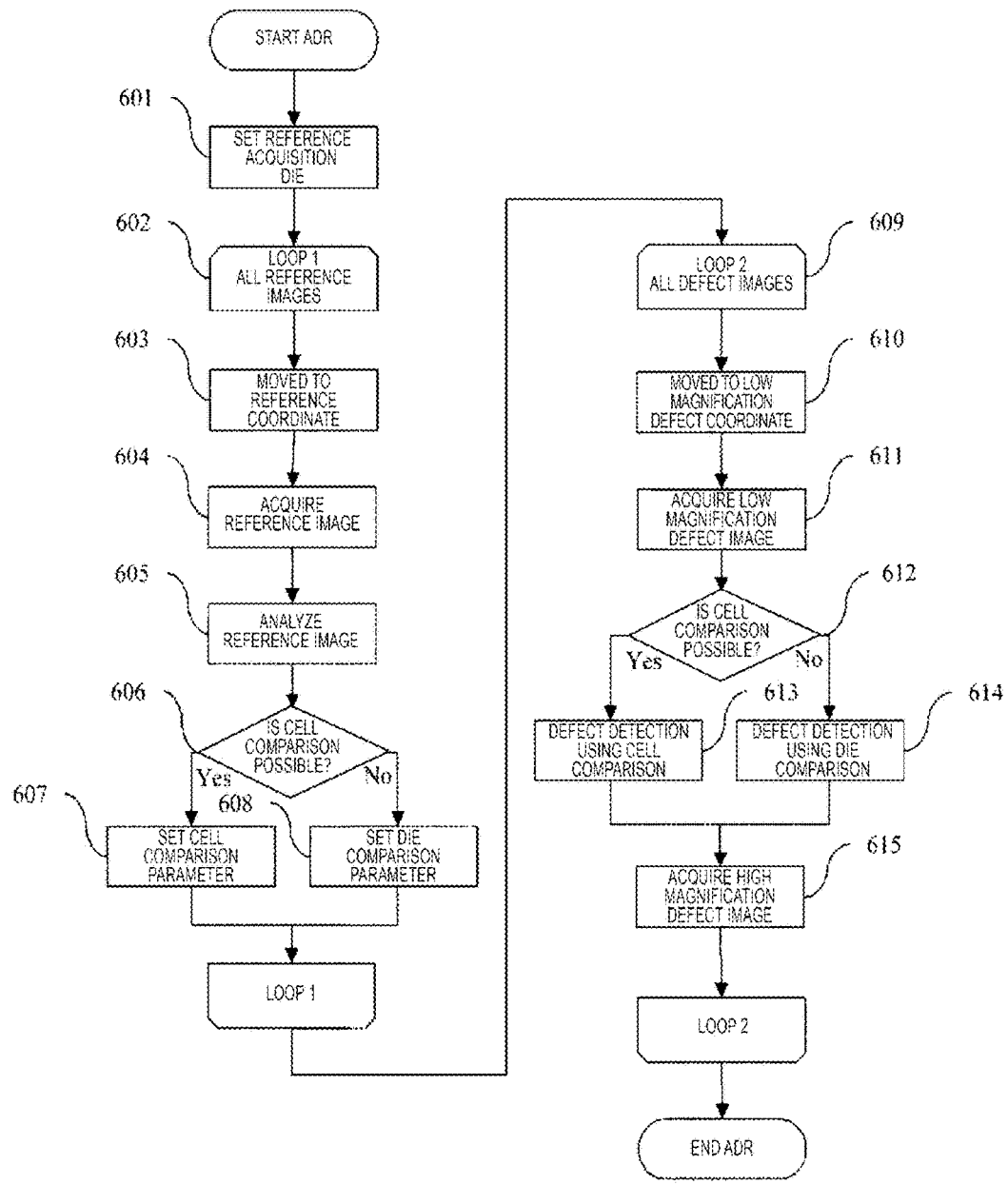

[Fig. 8]
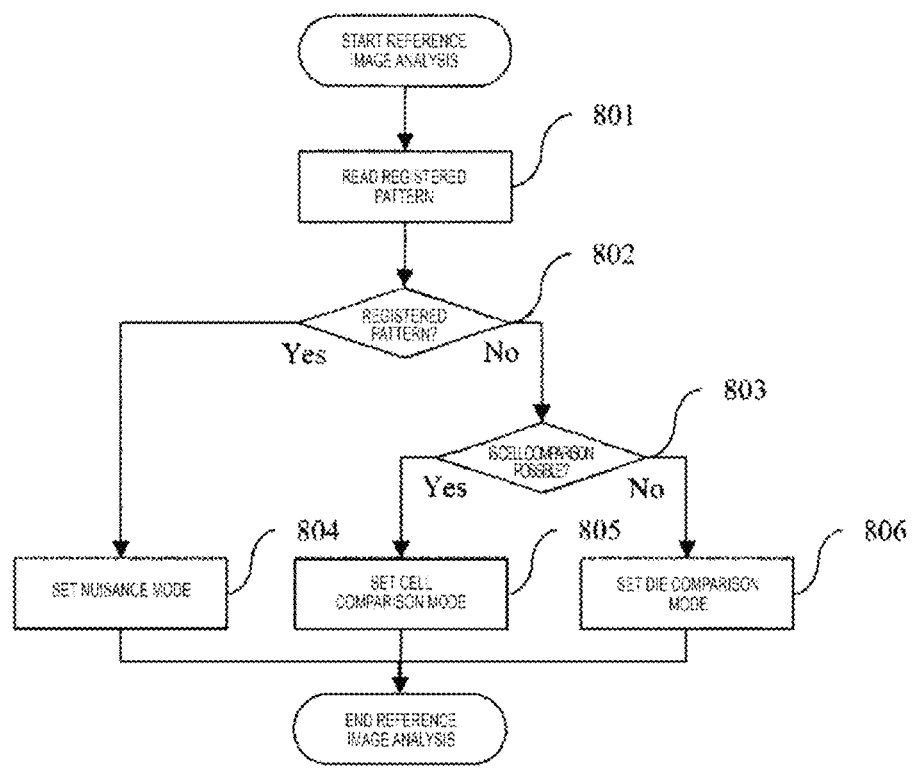

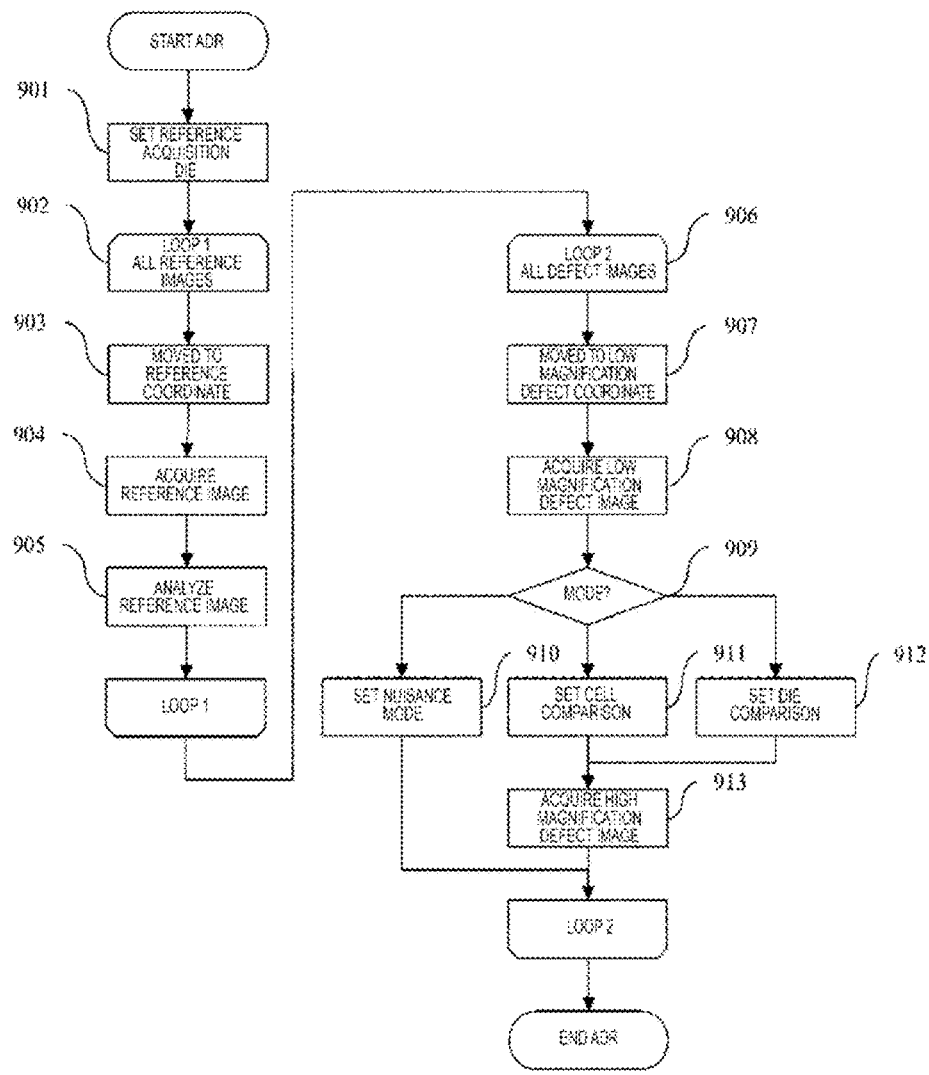
[Fig. 9]

DEFECT OBSERVATION DEVICE AND DEFECT OBSERVATION METHOD

TECHNICAL FIELD

The present invention relates to a defect observation device and a defect observation method used for a semiconductor manufacturing process.

BACKGROUND ART

In a semiconductor manufacturing process, in order to secure a high yield, it is important to find defects generated in the manufacturing process at an early stage and to take countermeasures. A scanning electron microscope (SEM) type defect observation device is a device for observing a defect generated in, for example, a semiconductor manufacturing process, and is a device for observing an image of a defect coordinate detected by a higher-rank defect inspection device with higher image quality than in the higher-rank defect inspection device. The higher-rank defect inspection device is, for example, an optical defect inspection device. Specifically, first, a sample stage is moved to the defect coordinate output from the higher-rank defect inspection device, and a defect which is an observation target is imaged at a low magnification to the extent of being included in a field of view. Next, the defect coordinate is detected from the captured low magnification image, the sample stage is moved so that the defect is located at the center of the field of view, or the imaging center is moved, and a high magnification image for observation at a high magnification suitable for defect observation is acquired. As mentioned above, the reason why a defect coordinate is detected with a low magnification image before a high magnification image for observation is acquired is that a defect coordinate output from a higher-rank defect inspection device includes an error within a range of a device specification, and thus it is necessary to perform a process for correcting the error in order for an SEM type defect observation device to acquire a defect image with high quality.

A process of automatically acquiring such a high quality defect image (high magnification image) is called an automatic defect review or automatic defect redetection (ADR). Accuracy of a coordinate for detecting a defect in a higher-rank defect inspection device, a physical characteristic of an observation target, or the like differs depending on the type of defect which is the observation target. Therefore, in the ADR, it is necessary to optimize acquisition conditions for a low magnification image for detecting a defect or acquisition conditions for a high magnification image for observing the defect, depending on the type of defect which is an observation target. The optimization is required to be performed by taking into consideration a balance between defect detection accuracy and throughput in the ADR. Thus, a plurality of defect detection methods, such as a defect detection method prioritizing improvement of defect detection accuracy or a defect detection method prioritizing improvement of throughput are prepared in the ADR, and are used depending on purposes. As a defect detection method, there are, for example, cell comparison in which adjacent pattern units are compared with each other with respect to repeated patterns in a single image, or die comparison in which an image of an inspection target location is compared by using an image of a position corresponding to an inspection target location in another die as a reference image.

PTL 1 discloses that "a defect is detected in a cell comparison method, then it is determined whether or not a defect is detected in the cell comparison method, and, as a result, in a case where it is determined that a defect cannot be detected in the cell comparison method, transition to a die comparison method in which a defect can be reliably detected occurs".

CITATION LIST

Patent Literature

PTL 1: JP-A-2007-305760 (specification of U.S. Patent Publication No. 2008/0067371)

SUMMARY OF INVENTION

Technical Problem

In recent years, defects exerting the influence on a yield have been diversified due to micronization of design patterns or complication of manufacturing processes, and thus difficulty of work of setting observation conditions optimal for the type of observation target defect has increased. Particularly, setting conditions for maintaining defect detection accuracy and also maximizing throughput in the ADR are highly difficult work since even an experienced operator repeats trial and error.

In the method disclosed in PTL 1, since it is determined whether or not a defect detection method using cell comparison is applied by using a low magnification defect image, in a case where a defect detection method using cell comparison can be employed, a reference image is not required to be acquired, and thus it is possible to improve throughput. However, in a case where the defect detection method using cell comparison cannot be employed, transition to the defect detection method using die comparison occurs, and then a reference image is acquired. Therefore, a throughput is reduced.

Specifically, in a case where transition to the defect detection method using die comparison occurs, since a low magnification defect image, a reference image, and a high magnification defect image are captured in this order, the stage is moved from a reference image acquisition position when the high magnification defect image is acquired, and thus a throughput is reduced. The movement of the stage from the reference image acquisition position is a process which is not performed in a case where all observation target locations are processed from the beginning in the defect detection method using die comparison. Thus, if a proportion of transition to the defect detection method using die comparison increases, as a result, a throughput is reduced more than in a case where all observation target locations are processed from the beginning in the defect detection method using die comparison. The extent of delay between a case where transition to the defect detection method using die comparison in the middle occurs and a case where all observation target locations are processed from the beginning in the defect detection method using die comparison differs depending on a specification of a defect observation device or an ADR condition, but, generally, if a proportion of transition to the defect detection method using die comparison exceeds approximately 20 to 30%, there are many cases where a throughput is reduced more than in a case where all observation target locations are processed from the beginning in the defect detection method using die comparison.

The proportion of transition to the defect detection method using die comparison depends on a positional relationship between a defect coordinate detected by a defect detection device and a manufacturing pattern, and thus cannot be expected before the ADR is performed. After the ADR is actually performed, it is proved that a case where all observation target locations are processed from the beginning in the defect detection method using die comparison can reduce processing time. Such a change in processing time hinders planned production activity, and thus there is the need for ADR leading to expectable and stable throughputs.

As in PTL 1, in a case where it is determined whether or not the defect detection method using cell comparison is applied by using a low magnification defect image, it may be wrongly determined whether or not the defect detection method using cell comparison is applied due to the influence of a defect region. If the defect detection method using cell comparison is wrongly applied in a case where the defect detection method using cell comparison cannot be applied, a region other than a defect region is erroneously detected as a defect, and thus defect detection accuracy is reduced.

An object of the present invention is to perform defect detection with stable throughput and high accuracy.

Solution to Problem

In order to achieve the above-described object, according to the present invention, a defect detection processing mode appropriate for detecting a defect from the defect image is determined by using a reference image, and a defect is detected from the defect image in the determined defect detection processing mode.

Advantageous Effects of Invention

According to the present invention, it is possible to provide a defect observation device which performs defect detection with stable throughput and high accuracy.

Objects, configurations, and effects other than those described above will become apparent through description of the following embodiments.

BRIEF DESCRIPTION OF DRAWINGS

FIG. 1 is a schematic diagram illustrating the entire configuration of an SEM type observation system in Example 1.

FIG. 2 is a schematic diagram illustrating an operation/analysis unit and a data flow in Example 1.

FIG. 3 is a block diagram related to a defect detection processing function in Example 1.

FIG. 4 is a flowchart of ADR with a defect detection mode optimization function in Example 1.

FIG. 6 is a flowchart of ADR with a defect detection mode optimization function in a reference image preceding acquisition method in Example 2.

FIG. 8 is a flowchart illustrating defect detection mode optimization in Example 3.

FIG. 9 is a flowchart of ADR with a defect detection mode optimization function corresponding to a nuisance mode in Example 3.

DESCRIPTION OF EMBODIMENTS

Figure 5A:
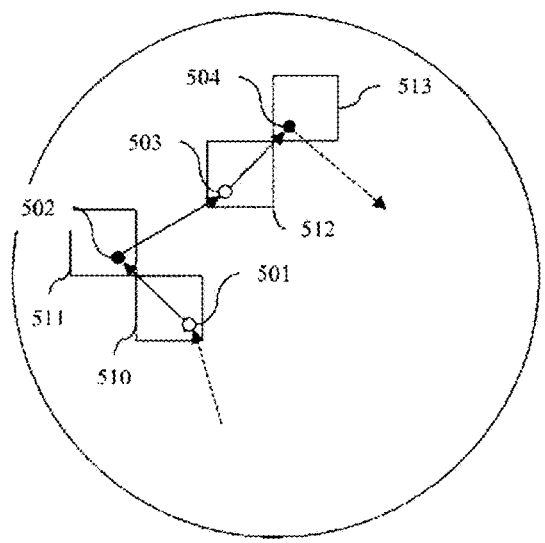
FIGS. 5A to 5B are schematic diagrams illustrating methods of selecting a reference image acquisition die in Example 2.

A description will be made of a configuration example of a defect observation method, a defect observation device, and a defect observation system in which highly accurate defect detection and high throughput are compatible for a sample in which an observation target suitable for a defect detection method using cell comparison and an observation target suitable for a defect detection method using die comparison are mixed with each other. A defect observation system described below is an example of the present invention, and the present invention is not limited to embodiments described below.

In the present specification, the "defect observation device" is a device which captures an image of a sample by using a charged particle beam, and includes devices detecting a defect by comparing a plurality of images with each other in a broad sense. The defect observation device will be also referred to as a defect review device in some cases. The "defect observation system" is a system in which the defect observation device is connected to other devices via a network or the like, and includes systems formed of the defect observation device in a broad sense.

As a configuration example of the defect observation system including the defect observation device, a description will be made of an example of acquiring a defect image through ADR in an SEM type defect observation device, but a configuration of the system is not limited thereto, and some or all devices forming the defect observation system may be formed of different devices. For example, an ADR process in the present example may be performed by an ADR processing device, an image management device, or a recipe management device, connected to the SEM type defect observation device via a network, and may be performed by a central processing unit (CPU) mounted in a versatile computer which is a constituent element of the system according to a program executing a desired calculation process. An existing device may be upgraded by using a storage medium recording the program thereon.

In the present specification, a "defect" is not limited to a foreign substance, and indicates observation target objects such as a material defect of a sample, a structure defect, a shape change of a manufacturing pattern, and a luminance change in a broad sense. In the present specification, a "defect image" includes not only an image as a defect observation target and an image of a true defect, but also images of defect candidates or images of pseudo-defects. A "reference image" is a criterion image used for comparison with a defect image in order to extract a defect, and indicates an image of a normal region, that is, a region in which it is estimated that there is no defect. A "defect coordinate" and a "reference coordinate" respectively indicate coordinate positions of representative points representing positions where a defect image and a reference image are acquired. Since portions described as "high magnification" and "low magnification" are relatively "high magnification" or "low magnification" in most cases, the terms "high magnification" and "low magnification" are used as representative examples, and do not indicate absolute magnifications. Though rare, there are cases where magnifications of "high magnification" and "low magnification" are reversed.

Hereinafter, with reference to the drawings, Examples of the present invention will be described in detail.

Example 1

An SEM type defect observation device is a device which acquires a high image quality SEM image corresponding to a defect coordinate under conditions appropriate for observation or analysis by using the defect coordinate detected by a defect inspection device such as an optical or SEM type inspection device as input information. As input information for the SEM type observation device, not only a defect coordinate detected by the defect inspection device but also coordinate information of an observation point extracted through simulation based on design layout data may be used.

FIG. 1 is a schematic diagram illustrating the entire configuration of an SEM type observation system in the present example. An SEM type defect observation device 118 illustrated in FIG. 1 includes a scanning electron microscope (SEM) which is means for capturing an SEM image, and an information processing device. The SEM type defect observation device 118 may include an optical microscope 117. The SEM includes an electron optical system which detects a secondary particle 108 generated from a sample 105 when the sample is irradiated with an electron beam; a stage 106 which moves a sample stand holding the sample which is an observation target in an XY plane; an electron optical system control unit 110 which controls various optical elements included in the electron optical system; an A/D conversion unit 111 which quantizes an output signal from a secondary particle detector 109; and a stage control unit 112 which controls the stage 106. The electron optical system is formed of optical elements such as an electron gun 101, a lens 102, a scanning deflector 103, an objective lens 104, and the secondary particle detector 109. The information processing device of the SEM type defect observation device 118 includes a general control unit 113 which controls both of the SEM and the information processing device; an image processing unit 114 which generates an image on the basis of a signal from the A/D conversion unit, and performs image analysis for extracting or classifying a defect by analyzing the image; an operation unit 115 which is used for a user to operate the device via a display, a keyboard, a mouse, and the like; and a storage device 116 such as a memory or a hard disk holding an acquired image or the like.

A primary electron beam 107 emitted from the electron gun 101 which converges due to the lens 102 is deflected by the scanning deflector 103, then converges due to the objective lens 104, and is subsequently applied to the sample 105. The secondary particle 108 such as a secondary electron or a reflected electron is generated from the sample 105 irradiated with the primary electron beam 107, depending on a shape or a material of the sample. The generated secondary particle 108 is detected by the secondary particle detector 109, and is then converted into a digital signal by the A/D conversion unit 111. An output signal from the secondary particle detector, converted into a digital signal will be referred to as an image signal in some cases. The output signal from the A/D conversion unit 111 is output to the image processing unit 114, so as to form an SEM image. The device may include other lenses, electrodes, or detectors, some configurations thereof may be different from the above-described configuration, and a configuration of the charged particle optical system is not limited thereto.

The image processing unit 114 performs various image analysis processes, for example, an ADR process of executing image processing such as defect detection by using a generated SEM image, or an automatic defect classification (ADC) of automatically classifying defects by type. The SEM type observation device of the present example can acquire images of observation targets at a plurality of different magnifications. For example, observation can be performed by changing a magnification as a result of changing a scanning range of the scanning deflector 103.

The electron optical system control unit 110 controls the optical elements of the electron optical system, such as the lens 102, the scanning deflector 103, and the objective lens 104. The stage control unit 112 controls the stage 106 so as to control a position of the sample. The general control unit 113 is a control unit which generally controls the entire SEM type observation device, analyzes input information from the operation unit 115 provided with a display, a keyboard, a mouse, and the like, and the storage device 116, so as to control the electron optical system control unit 110, the stage control unit 112, the image processing unit 114, and the like, and outputs a process result to a display portion included in the operation unit 115 or the storage device 116 as necessary.

A process performed by the image processing unit 114 may be realized by hardware formed of a dedicated circuit board, and may be realized by software executed by a computer connected to the defect observation device. In a case where the process is realized by the hardware, the hardware may be formed by integrating a plurality of calculators performing the process into a wiring board, a semiconductor chip, or a package. In a case where the process is realized by the software, the process may be realized by mounting a high speed CPU on the image processing unit 114, and executing a desired calculation process according to a program.

As an example of the defect observation system, FIG. 1 illustrates an example in which the SEM type defect observation device 118, a recipe management device 120, and a defect information database 121 are connected to each other via a local area network (LAN) 119. An image acquired by the SEM type defect observation device 118 is preserved in the defect information database 121. Other information regarding a defect, for example, defect image capturing conditions or detected defect coordinate is preserved in the defect information database 121. The recipe management device 120 acquires defect information required to create a recipe from the defect information database 121, performs calculation processes including image processing, and creates a recipe recording conditions or procedures for performing an ADR or ADC process. Parameters used for the calculation processes, the created recipe, or the like may be preserved in a storage device built into the recipe management device, or the defect information database. As mentioned above, the "defect information" includes information regarding a defect, such as a coordinate of the defect detected by the inspection device, an image captured by the inspection device, and an analysis result obtained by using an analysis function of the inspection device, or a coordinate of a defect redetected by the defect observation device, an image captured by the defect observation device, and an analysis result obtained by using an analysis function of the defect observation device.

FIG. 2 illustrates an example of a detailed diagram of the general control unit 113, the operation unit 115, and the storage device 116 illustrated in FIG. 1. Here, an operation/analysis unit 201 is an integration of the general control unit 113 and the operation unit 115 illustrated in FIG. 1. The operation/analysis unit 201 is formed of a plurality of functional blocks realized by a CPU incorporated into the general control unit 113 executing a predetermined program in response to an operation instruction from the operation unit 115. As mentioned above, the present example is not limited to a configuration in which the general control unit 113 as illustrated in FIG. 1 is incorporated into the SEM type observation device, and the operation/analysis unit 201 illustrated in FIG. 2 may be configured separately from the SEM type observation device illustrated in FIG. 1, and the constituent elements illustrated in FIGS. 1 and 2 may be connected to each other via a network. In a case where the constituent elements illustrated in FIG. 2 are incorporated into the defect observation system illustrated in FIG. 1, a defect data storage portion 202, an image data storage portion 203, an analysis parameter storage portion 204, and an analysis result data storage portion 205 may be integrated into the storage device 116 illustrated in FIG. 1.

The defect data storage portion 202 stores defect information such as a defect coordinate. The image data storage portion 203 stores a defect image captured by the SEM type observation device. The analysis parameter storage portion 204 stores processing conditions such as ADR conditions and ADC conditions used for image acquisition or image analysis, and thus a plurality of conditions can be reproduced. A process result is stored in the analysis result data storage portion 205.

As another Example, the function of the operation/analysis unit 201 may be realized by the recipe management device 120 of the SEM type defect observation system illustrated in FIG. 1. The defect data storage portion 202, the image data storage portion 203, the analysis parameter storage portion 204, and the analysis result data storage portion 205 may be realized by the defect information database 121 of the SEM type defect observation system illustrated in FIG. 1.

FIG. 3 illustrates an example of a functional block diagram for performing a defect detection process described below. In the functional block diagram in FIG. 3, for convenience of description, functions corresponding to the following Example are illustrated, but only these some functions may be installed in the device. As an example, such a functional block is installed in the general control unit 113 and the image processing unit 114.

First, an image generation unit 300 generates an image on the basis of a signal from the A/D conversion unit 111. The image generation unit 300 generates a low magnification defect image and a reference image, and the order of acquiring such images will be described later with reference to FIG. 4. A defect image is an image of a region including coordinates of defect candidates, and a reference image is a criterion image which includes the same field of view as that of the defect image and on which there is no defect. It can be said that the reference image is an image of a region in which a pattern having the same shape as that of a pattern included in a defect image in a die which is different from a die where the defect image is acquired is formed. The "reference image" is frequently acquired at the same magnification as that of a defect image, and will thus be referred to as a low magnification reference image in some cases.

Next, a cell/die comparison mode determination processing unit 302 analyzes a reference image 301 so as to determine a defect detection mode suitable for detecting a defect according to a pattern included in the reference image. Specifically, in a case where a predetermined determination criterion is satisfied, a defect detection mode using cell comparison is employed, and, in a case where the determination criterion is not satisfied, a defect detection mode using die comparison is employed. Here, it is assumed that a determination criterion for employing a cell comparison mode and a die comparison mode is determined in advance. Alternatively, a user may adjust a determination criterion. As the determination criterion, it may be used whether or not there is a specific periodicity in a pattern included in a reference image. In other words, the periodicity of a repeated pattern included in a reference image is determined, and, in a case where there is a specific or more periodicity, the defect detection mode using cell comparison is employed, and, in a case where there is no specific or more periodicity, the defect detection mode using die comparison is employed.

In a case where a mode determination result 303 in the cell/die comparison mode determination processing unit 302 is the defect detection mode using cell comparison, cell comparison is performed in which repeated patterns are compared with each other with respect to repeated patterns in a single image. In the defect detection mode using cell comparison, more specifically, a low magnification defect image is divided into a plurality of regions by using the periodicity of the repeated patterns, the separate regions are combined with each other so that a reference image in which there is no defect region is synthesized, and a difference between the low magnification defect image and the synthesized reference image is extracted so that a defect region is specified. Since the reference image is generated from the low magnification defect image, there is an advantage in that the defect detection mode using cell comparison is hardly influenced by a difference between image qualities of a low magnification defect image and a reference image, caused by a change in an imaging condition, a difference between image qualities of a low magnification defect image and a reference image, caused by a change in a sample charging situation, or manufacturing tolerance of manufacturing patterns at a low magnification defect image acquisition position and a reference image acquisition position.

On the other hand, in a case where the mode determination result 303 in the cell/die comparison mode determination processing unit 302 is the defect detection mode using die comparison, die comparison is performed in which an image of a position corresponding to an inspection target location in another die is compared with a defect image of the inspection target location as a reference image. More specifically, positioning is performed so that patterns other than defect regions of an acquired defect image and a reference image match each other, luminance correction is performed so that luminance distributions of the patterns other than the defect regions of the defect image and the reference image match each other, a subtraction process is performed in a state in which the positioning and the luminance correction are performed, and a difference between the defect image and the reference image is extracted so that a defect region is specified. A rotation correction process may be performed in addition to the processes depending on characteristics of a device or a sample.

General defect detection algorithms using cell comparison and die comparison are as described above, but defect detection algorithms using cell comparison and die comparison to which the present invention is applied are not limited to the above-described algorithms.

Generally, a design rule is strict in most cases for a region formed of repeated patterns to which the defect detection method using cell comparison is applicable, and thus it is desirable to detect a minute change of a manufacturing pattern as a defect candidate. In contrast, for a region which is not formed of repeated patterns and for which the defect detection method using die comparison is suitable, there are many peripheral circuit regions or the like, and thus a design rule is not relatively strict compared with repeated patterns as cell comparison targets. Therefore, allowable manufacturing tolerance is relatively large. Thus, a minute change in a manufacturing pattern is not a detection target, and a relatively large defect such as a foreign substance is a detection target in most cases.

A defect detection parameter setting unit 304 sets defect detection parameters 305 on the basis of the mode determination result 303. In the present example, the defect detection parameters 305 include defect detection parameters optimized for each executed defect detection mode in addition to the defect detection modes. Specifically, the defect detection parameters 305 include a noise removal intensity in image processing, a threshold value for regarding defect candidates of a specific size or less as noise with respect to defect candidates extracted on the basis of a difference between a low magnification defect image and a reference image, a threshold value for regarding defect candidates of a specific luminance difference or less as noise with respect to defect candidates detected on the basis of a difference between a low magnification defect image and a reference image, and the like. In the present example, not only the defect detection modes but also parameters regarding such defect detection sensitivity may be setting targets. Since other defect detection parameters can be set so as to correspond to a determined defect detection mode, it is possible to detect a defect by using optimal parameters for each defect detection mode.

As mentioned above, in addition to a defect detection mode set by analyzing a reference image, optimal defect detection parameters are set according to the set defect detection mode, and thus it is possible to realize highly accurate defect detection corresponding to various manufacturing patterns or various defect types.

A defect detection processing unit 306 extracts a defect coordinate 308 by using the defect detection parameters 305 including the defect detection mode and the parameters set according to the mode, the reference image 301, and a low magnification defect image 307. Here, in a case where the defect detection method using cell comparison is applied, as a reference image can be synthesized from a low magnification defect image, the reference image 301 may not be used.

In a case where whether or not the defect detection method using cell comparison is applied is determined on the basis of a low magnification defect image, and the defect detection method using cell comparison is employed, acquisition of a reference image is omitted, and thus a reference image cannot be used. However, in the present example, acquisition of the reference image 301 is not omitted, and thus the reference image 301 can be effectively used in order to improve defect detection accuracy. For example, a common region may be determined as being a defect region, and the common region being common to a defect candidate which is detected on the basis of a difference between a synthesized image synthesized from the low magnification defect image 307 and the low magnification defect image 307, and a defect candidate which is detected on the basis of a difference between the reference image 301 obtained by actually imaging a location estimated as a normal pattern and the low magnification defect image 307. In other words, a combination between a result detected in the defect detection mode using cell comparison and a result detected in the defect detection mode using die comparison may be used as a final defect detection result.

As another example, a synthesized image synthesized from the low magnification defect image 307 may be compared with the reference image 301 obtained through actual imaging, and a difference therebetween may be determined as being not a defect but a noise component so as to be excluded from defect candidates. As mentioned above, even in a case where a defect is detected by using cell comparison, the defect is detected by also using an actually captured reference image, and thus it is possible to improve defect detection accuracy.

FIG. 4 is a flowchart of ADR including a defect comparison mode determination process in the present example.

First, a sample is moved to a coordinate for acquiring a reference image (401), and then the reference image is acquired by the SEM (402).

Next, the mode determination processing unit 302 analyzes the acquired reference image so as to determine a defect detection mode (403). Since the reference image analysis process (403) is a process for determining a defect detection mode, the process may be completed until defect detection is performed (406) on the basis of the defect detection mode, and may be performed in parallel to low magnification defect coordinate movement (404) or low magnification defect image acquisition (405). The reference image analysis process (403) is a process which is independent from the low magnification defect coordinate movement (404) or the low magnification defect image acquisition (405), and thus a throughput can be improved through parallel processes.

Next, the sample is moved to a coordinate where a low magnification defect image is acquired by the stage (404), and a low magnification defect image is acquired by the SEM (405). It is determined whether or not the defect detection method using cell comparison can be applied on the basis of the reference image analysis result (403) (406). In the present example, since a single reference image corresponds to a single low magnification defect image, the image processing unit 114 determines a defect detection mode on the basis of the reference image corresponding to the low magnification defect image. Therefore, it is possible to switch between defect detection modes to be applied for each low magnification defect image.

In the present example, since a defect detection mode is determined by analyzing a reference image (403), and this method is advantage in that there is no influence of defect region compared with a method of determining a defect detection mode by analyzing a low magnification defect image. Since the low magnification defect image is an inspection target image, there is a probability that the presence of a defect may influence a determination result in a case where a defect detection mode is determined by using the low magnification defect image. Particularly, in a case where a defect region is relatively large with respect to a defect image, or a defect region is cyclic, this has an adverse effect on defect detection. Therefore, it is possible to determine a more accurate mode by determining a defect detection mode on the basis of a reference image which is different from an actual inspection target.

In a case where the defect detection method using cell comparison can be applied, the defect detection parameter setting unit 304 applies defect detection parameters for cell comparison (407), and the defect detection processing unit 306 performs defect detection according to the defect detection method using cell comparison (409). As described in FIG. 3, in a case where defect detection is performed according to the defect detection method using cell comparison (409), a defect can be detected by using only the low magnification defect image (405) without using the reference image (402), but it is possible to realize more accurate and stable defect detection by also using the reference image (402).

In a case where the defect detection method using cell comparison cannot be applied, the defect detection parameter setting unit 304 applies defect detection parameters for die comparison (408), and the defect detection processing unit 306 performs defect detection according to the defect detection method using die comparison (410). In the defect detection using the die comparison method, the captured reference image (402) is compared with the low magnification defect image (405), and a defect therebetween is detected as a defect region.

As described in FIG. 3, defect detection accuracy is preferably improved and stabilized by optimizing defect detection parameters for each defect detection mode. This is indicated by setting defect detection parameter appropriate for the defect detection mode using cell comparison (407) and setting defect detection parameters appropriate for the defect detection mode using die comparison (408) in the flowchart illustrated in FIG. 4. In other words, it is possible to improve and stabilize defect detection accuracy by setting defect detection parameters appropriate for a defect detection mode (407 or 408) and performing defect detection according to the defect detection method using cell comparison (409) or performing defect detection according to the defect detection method using die comparison (410).

A high magnification defect image is acquired by the SEM at a magnification appropriate for observation at a defect coordinate detected through cell comparison or die comparison (411). Generally, a high magnification defect image is frequently acquired at a higher magnification than a magnification of a low magnification defect image. However, a high magnification defect image may be acquired at a magnification which is equal to or lower than a magnification of a low magnification defect image. Imaging conditions for a high magnification defect image may be exchanged with imaging conditions for a low magnification image. For example, in order to improve a resolution of a high magnification defect image, a total number of frames is increased, or a focus condition is changed. According to the present example, the stage may stand still until a high magnification defect image is acquired from acquisition of a low magnification defect image with respect to a single defect. Since the stage is not required to be moved, a throughput can be increased by reducing time required for the stage to be moved.

According to the above-described Example, since a defect detection mode is determined by using a reference image, it is possible to perform highly accurate defect detection with a stable throughput even for a sample with a small number of repeated patterns. Since a defect detection mode is determined on the basis of a reference image with a normal pattern, it is possible to determine a more accurate mode without being influenced by a defect region.

There may be a method in which a pattern of a sample is predicted on the basis of design information, and a defect detection mode is set, but, generally, a management division of design information is frequently different from a management division of a defect observation device, and it is typically difficult to introduce a system in which a defect observation device handles design information from the viewpoint of security management. Even in a case where design information can be acquired, it is necessary to select design information appropriate for defect observation from among a large volume of design information, specifically, design information of a process which can be confirmed when an image is captured by the defect observation device without excess or deficiency, and thus an operator is required to have knowledge of a certain level or higher. A defect coordinate detected by the defect inspection device includes an error within a specification range, and thus it is hard to say that determination accuracy is high in a case where the defect coordinate including the error is matched with design information, and whether or not the defect detection method using cell comparison is applied on the basis of the design information. In a case where a defect is detected according to the defect detection method using cell comparison for a sample to which the defect detection method using cell comparison cannot be applied on the basis of a wrong determination result, a normal manufacturing pattern is erroneously detected as a defect, and thus a reduction in defect detection accuracy is problematic. Calculation processing cost using design information is also problematic, and there are many cases in which comprehensive defect observation time including time for a design information analysis process which is a preprocess is long, and thus this is hardly put into practical use. In contrast, according to the method described in the present example, a defect detection mode can be set without using design information, and thus it is possible to determine a defect detection mode simply with high accuracy.

Example 2

In the present example, a description will be made of an example of a method of a defect observation method for realizing improvement of a throughput compared with the method described in Example 1. Configurations illustrated in FIGS. 1 to 3 and the content described in FIG. 4 are the same as those in the present example, and thus description thereof will be omitted.

FIG. 5 is a schematic diagram for explaining a method of selecting a die in which a reference image is acquired. In FIG. 5, an outer circle indicates a wafer used in a semiconductor manufacturing process. A plurality of dies are formed on the wafer, and FIG. 5 illustrates representative dies 510 to 516. The reference numerals 501 to 509 indicate imaging positions (more specifically, for example, center coordinates of imaging regions) in the dies, black circles (502, 504, 508, 509) indicate defect coordinates, and white circles (501, 503, 506, and 507) indicate reference coordinates.

FIG. 5(*a*) is a schematic diagram illustrating a case where a reference image is acquired in a die adjacent to a defect image acquisition die. In the present example, a reference image is first acquired, then a low magnification defect image is acquired, a defect is detected, and a high magnification defect image is acquired with a detected defect coordinate as the image center. A reference image being first acquired is aimed at reducing the number of stage movements for which processing time is long and which causes a throughput reduction. For example, in a case where a low magnification defect image, a reference image, and a high magnification defect image are acquired in this order, the stage is moved three times until a high magnification defect image of a single defect is acquired. In contrast, as in the present example, if a reference image, a low magnification defect image, and a high magnification defect image are acquired in this order, the stage is not required to be moved when the high magnification defect image is captured, and thus the number of stage movements can be reduced to two.

In FIG. 5(*a*), a reference image corresponding to an N-th observation point is acquired at the reference coordinate 501 included in the die 510 adjacent to the die 511 including the N-th point defect coordinate 502. Next, a low magnification defect image is acquired at the defect coordinate 502 of the N-th observation point. In the same manner for a (N+1)-th observation point, a reference image is acquired at the reference coordinate 503 included in the die 512 adjacent to the die 513 including the (N-th) defect coordinate 504, and a low magnification defect image is acquired at the defect coordinate 504. As mentioned above, in a case where a reference image is acquired in a die adjacent to a die including a defect coordinate, a stage movement distance for each observation point which is required to acquire a reference image may be approximated by (Equation 1) with a die size as (x,y).

$$L_1(x,y) = \sqrt{x^2+y^2}$$ [Equation 1]

Figure 5B:
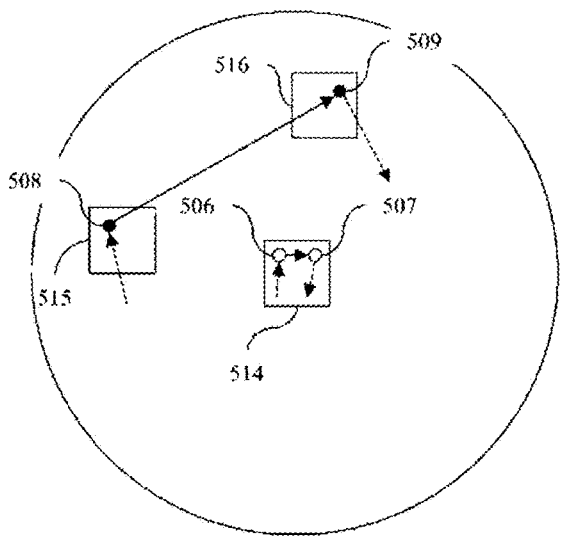

FIG. 5(b) is a schematic diagram illustrating a case where reference images are collected and precedingly acquired in a designated die. In this method, coordinates in a die of all observation target defect coordinates as defect candidates are projected onto a designated die so as to be used as reference coordinates, and images of the reference coordinates in the designated die are collected as reference images and are precedingly acquired. Typically, a defect coordinate is expressed by the die origin indicating a position of a die including a defect in the entire sample, and an in-die coordinate indicating at which position a defect is present in the die with a predetermined position in the die as a reference. Here, the die origin is a coordinate indicating a position used as a reference in each die. The "die origin" mentioned here may be a coordinate obtained by adding an offset to the die origin. Each die may be identified by a die number specific to each die. In this method, a die number indicating a die including a defect coordinate is replaced with a die number indicating a designated die, and a position of the same in-die coordinate as the defect coordinate in the designated die is selected as a reference coordinate.

In FIG. 5B, the die 514 in the vicinity of the wafer center is designated as a die in which a reference image is acquired. In the die 514 designated in order to acquire a reference image, a reference image of the reference coordinate 506 corresponding to an N-th observation point and a reference image of the reference coordinate 507 corresponding to an (N+1)-th observation point are sequentially acquired in this order from a first observation point.

Here, a die in which a reference image is acquired may be designated by a user, and may be automatically selected. In a case where a reference image is automatically selected, it is preferable to automatically select a die which is located near the wafer center and has no defect.

A die being preferably located near the wafer center is aimed at preventing a distance between a defect image and a reference image from excessively increasing, since, if a distance between a low magnification defect image and a reference image is long, pattern manufacturing tolerance tends to increase. When a wafer center portion is compared with a wafer outer circumferential portion, the wafer outer circumferential portion generally tends to have large pattern manufacturing tolerance. Thus, in a case where a die is automatically selected, the die is preferably preferentially selected from the wafer center which can be expected to have small manufacturing tolerance. In a case where distributions of manufacturing tolerance in a wafer surface are different from each other, a region may be divided into a plurality of regions according to expected distributions of manufacturing tolerance, and a die in which representative manufacturing tolerance of each region is regarded to be reflected may be selected as a die in which a reference image is acquired.

Here, the reason why a die preferably has no defect is that, in a case where there is a defect in a die in which a reference image is acquired, a reference image of the defect is required to be acquired by moving the stage to another die, and thus a stage movement distance is increased.

Specifically, with respect to a defect coordinate detected by an inspection device, a review target defect coordinate may be selected through sampling, and a die in which the selected review target defect coordinate is not present may be selected as a die in which a reference image is acquired. In a case where there is a die having no defect, the die having no defect is selected, and thus it is possible to minimize a stage movement distance. Even in a case where a die having a defect is selected, a plurality of adjacent dies are selected, and thus it is possible to prevent a stage movement distance from being increased.

As mentioned above, in a case where a die in which reference images are collected and are precedingly acquired is automatically selected, it is preferable to select a die which is located near the wafer center and has no defect. In a case where there is no die having no defect, a plurality of dies in which reference images are collected and are precedingly acquired may be selected. Regarding a method of selecting a plurality of dies, the wafer center is preferably selected for the above-described reason, and a die is preferably selected so that a stage movement distance is short when a reference image is acquired. As an algorithm determining a path for shortening a stage movement distance, there is the algorithm solving a traveling salesman problem, but this is only an example.

A stage movement distance for each observation point in a case where reference images are collected and are precedingly acquired in a single designated die may be approximated by (Equation 2) with the number of observation points as N.

$$L_2(x, y) = \sqrt{\frac{xy}{N}}$$ [Equation 2]

In a case where there is no die having no defect, two dies adjacent to each other are regarded to be selected, and a stage movement distance for each observation point may be approximated by Equation 3.

$$L_3(x, y) = \sqrt{\frac{2xy}{N}}$$ [Equation 3]

For example, if a die size is 3×3 mm, and the number of observation points is 500, this leads to $L_1 \approx 4.24$ mm, $L_2 \approx 0.13$ mm, and $L_3 \approx 0.26$ mm, and reference images are collected and are precedingly acquired in a designated die so that a stage movement distance during acquisition of a reference image can be considerably reduced to 1/10 or less.

FIG. 6 is a flowchart illustrating a case where reference images are collected and are precedingly acquired in a designated die. First, a die in which reference images are acquired is set (601), and reference images are collected and are precedingly acquired in the set die (602). In a loop process of precedingly acquiring all reference images, first, movement to a reference coordinate is performed (603), and a reference image is acquired (604).

Next, an image analysis process for determining a defect detection mode is performed on the acquired reference image (605). The image analysis process (605) for determining a defect detection mode, a defect detection mode determination process (606) based on an analysis result, and a cell comparison parameter setting process (607) or a die comparison parameter setting process (608) based on a mode determination result may be completed by a cell comparison defect detection process (613) or a die comparison defect detection process (614) based on a defect detection mode determination result (612). Processes from the reference image analysis process (605) to the cell comparison parameter setting process (607) or the die comparison parameter setting process (608) are performed separately from the movement process (603) to a reference coordinate corresponding to the next observation point and the process (604) of acquiring a reference image at the reference coordinate, and thus parallel processes may be performed without waiting for other processes to be completed. Consequently, it is possible to improve a throughput in ADR. In other words, in a case where reference images are collected and are precedingly acquired, a defect detection mode is preferably determined within time required for the process of collecting and precedingly acquiring reference images, and thus it is possible to increase time used for the defect detection mode determination process compared with Example 1. Also in relation to this fact, the method of collecting and precedingly acquiring reference image is advantageous.

The reference images are collected and precedingly acquired, and low magnification defect images are sequentially acquired after an analysis process is performed on the acquired reference images or in parallel to the analysis process (609). First, movement to a low magnification defect image coordinate is performed (610), and a low magnification defect image is acquired (611). Next, a defect is detected on the basis of a defect detection mode determined by analyzing the precedingly acquired reference images (605), and defect detection parameters. Specifically, in a case where the defect detection method using cell comparison is employed, a defect is detected on the basis of defect detection parameters which are set as defect detection parameters appropriate for the defect detection method using cell comparison (607) according to the defect detection method using cell comparison (613). In a case where the defect detection method using cell comparison cannot be applied, the defect detection method using die comparison is employed. In a case where the defect detection method using die comparison is employed, a defect is detected on the basis of defect detection parameters which are set as defect detection parameters appropriate for the defect detection method using die comparison (608) according to the defect detection method using die comparison (614). Finally, an image of a detected defect coordinate is acquired as a high magnification defect image under conditions appropriate for observation or analysis (615). These procedures are repeatedly performed until all high magnification defect images are acquired (609).

As mentioned above, according to the present example, reference images are collected and are precedingly acquired in a predetermined die which is designated in advance, and thus it is possible to reduce a stage movement distance and thus improve a throughput. Since reference images are collected and are precedingly acquired in a designated die prior to acquisition of a low magnification defect image, it is possible to secure analysis process time for determining an appropriate defect detection mode on the basis of the reference images and thus to determine an accurate defect detection mode without reducing a throughput.

Example 3

In the present example, a throughput can be improved compared with the method described in Example 1. A description will be made of a defect observation method capable of also improving a throughput compared with Example 2. Configurations illustrated in FIGS. 1 to 3 and the content described in FIGS. 4 to 6 are the same as those in the present example, and thus description thereof will be omitted.

In Example 3, image analysis using a reference image is performed in detail, and thus a high magnification defect image processing time is reduced so that a throughput is improved. More specifically, in the present example, it is determined whether or not there is a pattern which is the same as or similar to a pattern which is registered in advance in a reference image, and a defect detection mode which is determined in advance so as to correspond to the registered pattern is selected according to a determination result. In other words, the methods described in Examples 1 and 2 and the method according to the present example are common to each other in that a defect detection mode is selected according to a pattern included in a reference image.

Figure 7A:
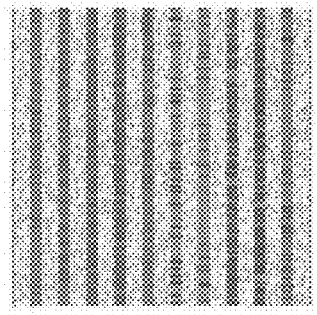
FIGS. 7A to 7C are schematic diagrams illustrating sample examples corresponding to each defect detection mode in Example 3.
Figure 7B:
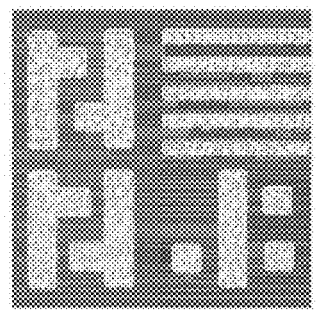

FIG. 7 illustrates examples of sample patterns corresponding to respective defect detection modes when a defect detection mode is determined by analyzing a reference image.

FIG. 7(*a*) illustrates an example of a reference image appropriate for the defect detection method using cell comparison, and the reference image excluding a defect region can be synthesized even from a low magnification defect image in which a defect is presented in the image since the periodicity of a predetermined value or more in the x direction is present. As described in Example 1, a defect can be detected from only a low magnification defect image without using a captured reference image, but it is possible to improve defect detection accuracy or stability by also using the captured reference image. FIG. 7(*a*) illustrates an example in which there is the periodicity in the x direction, but also in a case where there is the periodicity in the y direction or the periodicity in both of the x direction and the y direction, a reference image can be synthesized from a low magnification defect image by using the periodicity. Also in the present example, in the same manner as in Examples 1 and 2, a method of creating a reference image excluding a defect region from a low magnification defect image is not limited to the above-described method, and may employ other methods.

FIG. 7(*b*) illustrates an example of a reference image appropriate for the defect detection method using die comparison. In this case, since there is no periodicity of a predetermined value or more, the defect detection method using cell comparison cannot be applied. Therefore, a reference image is captured, and a defect is detected on the basis of a difference between a low magnification defect image and the reference image.

FIG. 7(*c*) illustrates an example of a reference image corresponding to a nuisance mode which is newly added in Example 3. The nuisance mode is a mode which is selected in a case where an amount of information to be acquired is smaller than in a normal mode. For example, a high magnification image of a defect is unnecessary, but the mode is effective when it is sufficient to know the number of defects. More specifically, in the nuisance mode, in a case where importance of an observation target defect is low, acquisition of a high magnification defect image is omitted, or a defect region is cut out of a low magnification image, and a high magnification image is created through digital zooming. In other words, in this mode, in a case where importance of an observation target defect is low, improvement of a throughput is prioritized more than acquisition of a high resolution image.

Figure 7C:
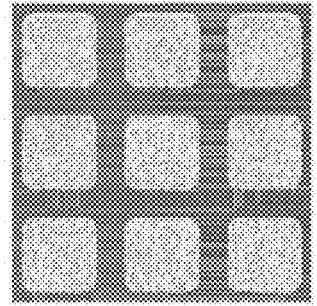

FIG. 7(c) illustrates a case of a dummy pattern, but a process corresponding to the nuisance mode may be executed by registering a pattern which is desired to be processed in the nuisance mode in advance. As targets of the nuisance mode, in addition to a dummy pattern, for example, there is a specific pattern in which a defect desired to be excluded from an observation target is generated. For example, in a case where a defect generated in a specific manufacturing pattern or pattern deformation caused by manufacturing tolerance is desired to be processed in the nuisance mode, a specific manufacturing pattern in which a defect is generated or pattern deformation occurs due to manufacturing tolerance may be registered in advance as a nuisance pattern.

FIG. 8 is a flowchart illustrating a process in which a reference image is analyzed, and thus a defect detection mode is determined. Examples 1 and 2, a defect detection mode is determined as two types of modes such as the defect detection method using cell comparison and the defect detection method using die comparison, but is determined, in Example 3, as three types of modes including the nuisance mode.

First, a registered nuisance pattern is read (801), and it is determined whether or not the read nuisance pattern is present in a reference image (802). In a case where the nuisance pattern is present in the reference image, the nuisance mode is set (804). In a case where the nuisance pattern is not present in the reference image, it is determined whether or not the defect detection method using cell comparison can be applied to a pattern (803). In a case where it is determined that the defect detection method using cell comparison can be applied to the pattern, a defect detection mode is set to the defect detection method using cell comparison (805), and, in a case where it is determined that the defect detection method using cell comparison cannot be applied to the pattern, a defect detection mode is set to the defect detection method using die comparison (806).

Here, setting of each defect detection mode includes setting parameters appropriate for each defect detection mode. For example, in the defect detection method using cell comparison, defect detection is performed by using high sensitivity defect detection parameters corresponding to a fine defect, and, in the defect detection method using die comparison, defect detection parameters are set which are appropriate for detecting a defect larger than a defect expected in a case where the defect detection method using cell comparison is applied. Alternatively, in the defect detection method using die comparison, manufacturing tolerance larger than manufacturing tolerance of a manufacturing pattern expected in a case where the defect detection method using cell comparison is applied is expected, and, as a result of comparing a reference image with a low magnification defect image, if a difference therebetween is smaller than the manufacturing tolerance, the difference may be excluded from defect candidates. A threshold value which is determined on the basis of the manufacturing tolerance may be set as a noise removal parameter. As mentioned above, since defect detection parameters appropriate for each defect detection mode are set, it is possible to improve defect detection accuracy or stability.

In the above-described example, the nuisance mode is described as an example, but, with respect to a defect of interest (DOI), a pattern in which a DOI easily occurs may be registered, and defect detection parameters appropriate for detecting a DOI may be set in a case where the registered pattern is present.

In the nuisance mode, re-imaging of a region within a field of view of a low magnification defect image at a higher magnification may be omitted. Improvement of a throughput can be prioritized by omitting capturing of a high magnification defect image and using a low magnification defect image as a high magnification defect image. As another example of the nuisance mode, a partial region may be cut out of a low magnification defect image by using a defect position detected on the basis of the low magnification defect image as the image center, the magnification of the cutout image may be increased through a digital zooming process, and a result thereof may be regarded as a high magnification defect image so that capturing of a high magnification defect image is omitted. In a case where defect detection is not necessary such as in a dummy pattern, an image obtained by cutting a portion with the maximum similarity between a registered pattern and a low magnification defect image as the image center through digital zooming may be used as a high magnification defect image, and capturing of a high magnification defect image may be omitted so that a throughput can be improved.

Such a defect detection process and an image cutting process can be performed separately from and in parallel to an imaging process on the next observation point, it is possible to make improvement of a throughput and acquisition of a high magnification defect image compatible by omitting a process of capturing a high magnification defect image.

FIG. 9 is a flowchart illustrating ADR for realizing improvement of a throughput by adding the nuisance mode to a defect detection mode. Since Example 3 prioritizes improvement of a throughput, in the same manner as in Example 2, a description will be made of an example of employing a method in which reference images are collected and are precedingly acquired in a designated die, but this method is only an example.

First, a die in which reference images are precedingly acquired is set (901). As described in Example 2, a die in which reference images are collected and are precedingly acquired may be designated by a user, but, in a case where a die is automatically selected, it is preferable to select a chip which is located near the wafer center and has no defect. Next, defect coordinates are projected onto the die in which reference images are collected and are precedingly acquired, and reference images are collected and are precedingly acquired in the designated die (902). Specifically, movement to a reference image acquisition coordinate is performed (903), a reference image is acquired (904), the acquired reference image is analyzed (905), and a defect detection mode is determined. The reference image analysis (905) can be performed separately from and in parallel to movement (903) to a coordinate for acquiring the next reference image or acquisition (904) of the next reference image, and thus it is possible to improve a throughput.

Since a result of analyzing a reference image is necessary in a defect detection mode determination process (909), it is sufficient to complete the defect detection mode determination process (909), and thus the method in which reference images are collected and are precedingly acquired is advantageous in that more time required for reference image analysis can be secured.

The reference images are collected and are precedingly acquired in the designated die (902), and then low magnification defect images are consecutively acquired (906). In the loop process (906) of consecutively acquiring low magnification defect images, first, movement to a low magnification defect image coordinate is performed (907), and a low magnification defect image is acquired (908). Next, on the basis of a defect detection mode determined by analyzing the reference image (905), a defect detection mode including defect detection parameters appropriate for the determined defect detection mode is set (909).

In a case where the nuisance mode is set (910), acquisition of a high magnification defect image is omitted, and thus it is possible to improve a throughput. Alternatively, as described above, a high magnification defect image may be cut out of a low magnification defect image through digital zooming. In a case where the defect detection method using cell comparison is set (911), defect detection is performed by using defect detection parameters appropriate for the defect detection method using cell comparison, and a high magnification defect image of a region indicated by a detected defect coordinate is captured (913). In a case where the defect detection method using die comparison is set (912), defect detection is performed by using defect detection parameters appropriate for the defect detection method using die comparison, and a high magnification defect image of a region indicated by a detected defect coordinate is captured (913). As mentioned above, defect detection parameters optimal for each defect detection mode are set on the basis of a result of analyzing a reference image, a defect is detected according to a defect detection method appropriate for an observation target, and thus it is possible to achieve both highly accurate defect detection and high throughput.

The present invention is not limited to the above-described Examples, and includes various modification examples. The above-described Examples have been described in detail for better understanding of the present invention, and are not limited to include all the above-described configurations. Some configurations of a certain Example may be replaced with configurations of other Examples, and configurations of other Examples may be added to configurations of a certain Example. The configurations of other Examples may be added to, deleted from, and replaced with some of the configurations of each Example.

Some or all of the above-described respective configurations, functions, processing units, and processing means may be designed as, for example, integrated circuits so as to be realized in hardware. The above-described respective configurations and functions may be realized in software by a processor analyzing and executing a program for realizing each function. Information regarding a program, a table, a file, and the like for realizing each function may be stored in a recording device such as a memory, a hard disk, or a solid state drive (SSD), or a recording medium such as an IC card, an SD card, or an optical disc.

A control line or an information line which is necessary for description is illustrated, and all control lines or information lines on a product may not necessarily be illustrated. It may be considered that almost all of the configurations are connected to each other.

REFERENCE SIGNS LIST

101: ELECTRON GUN, 102: LENS, 103: SCANNING DEFLECTOR, 104: OBJECTIVE LENS, 105: SAMPLE, 106: STAGE, 107: PRIMARY ELECTRON BEAM, 108: SECONDARY PARTICLE, 109: SECONDARY PARTICLE DETECTOR, 110: ELECTRON OPTICAL SYSTEM CONTROL UNIT, 111: A/D CONVERSION UNIT, 112: STAGE CONTROL UNIT, 113: GENERAL CONTROL UNIT, 114: IMAGE PROCESSING UNIT, 115: OPERATION UNIT, 116: STORAGE DEVICE, 117: OPTICAL MICROSCOPE, 118: SEM TYPE DEFECT OBSERVATION DEVICE, 119: LAN, 120: RECIPE MANAGEMENT DEVICE, 121: DEFECT INFORMATION DATABASE

201: OPERATION/ANALYSIS UNIT, 202: DEFECT DATA STORAGE PORTION, 203: IMAGE DATA STORAGE PORTION, 204: ANALYSIS PARAMETER STORAGE PORTION, 205: ANALYSIS RESULT STORAGE PORTION

501: N-TH POINT REFERENCE COORDINATE, 502: N-TH POINT DEFECT COORDINATE, 503: (N+1)-TH POINT REFERENCE COORDINATE, 504: (N+1)-TH POINT DEFECT COORDINATE, 506: N-TH POINT REFERENCE COORDINATE, 507: (N+1)-TH POINT REFERENCE COORDINATE, 508: N-TH POINT DEFECT COORDINATE, 509: (N+1)-TH POINT DEFECT COORDINATE, 510 TO 515: DIE

The invention claimed is:

1. A defect observation device comprising:
   a charged particle optical system that detects secondary particles obtained by irradiating a sample with a charged particle beam;
   an image processing unit that generates an image by using signals based on the secondary particles, and analyzes the image; and
   a stage that holds and moves the sample,
   wherein the image processing unit includes
   an image generation portion that generates a defect image which is an image of a region including coordinates of defect candidates, and a reference image which is an image including a region in which a pattern having the same shape as a shape of a pattern included in the defect image is formed in a die which is different from a die in which the defect image is acquired,
   a mode determination processing portion that determines a defect detection processing mode appropriate for detecting a defect from the defect image by using the reference image, and
   a defect detection processing portion that detects a defect from the defect image in the defect detection processing mode determined by the mode determination processing portion.

2. The defect observation device according to claim 1,
   wherein the defect detection processing mode includes a defect detection mode using cell comparison in which a defect is detected by comparing repeated patterns in the defect image with each other, and a defect detection mode using die comparison in which a defect is detected by comparing the defect image with the reference image.

3. The defect observation device according to claim 2,
   wherein the image processing unit combines a result detected in the defect detection mode using cell comparison with a result detected in the defect detection mode using die comparison so as to fix a final defect detection result.

4. The defect observation device according to claim 2,
   wherein the image processing unit determines a difference between a synthesized image which is synthesized on the basis of the repeated patterns in the defect image and the reference image as a noise component in the defect detection mode using cell comparison.

5. The defect observation device according to claim 1, wherein an image of a position detected by the defect detection processing portion is acquired again without moving the stage after the defect image is acquired.

6. The defect observation device according to claim 1, wherein parameters used for a process of detecting the defect can be set to correspond to the defect detection mode determined by the mode determination processing portion.

7. The defect observation device according to claim 1, wherein the reference image is acquired at positions where the coordinates of the defect candidates are projected onto a predetermined die which is designated in advance.

8. The defect observation device according to claim 1, wherein the mode determination processing portion determines a defect detection processing mode according to the presence or absence of a pre-registered pattern in the reference image.

9. The defect observation device according to claim 8, wherein, in a case where the registered pattern is present, a position detected by the defect detection processing portion is not imaged again.

10. The defect observation device according to claim 8, wherein, in a case where the registered pattern is present, an image of a partial region is cut out of the defect image, and an image having a magnification higher than a magnification of the defect image is generated by performing a digital zoom process on the cutout image.

11. A defect observation method of detecting secondary particles obtained by irradiating a sample with a charged particle beam, and generating an image by using signals based on the secondary particles, the method comprising:
    acquiring a defect image which is an image of a region including coordinates of defect candidates, and a reference image which is an image including a region in which a pattern having the same shape as a shape of a pattern included in the defect image is formed in a die which is different from a die in which the defect image is acquired;
    determining a defect detection processing mode appropriate for detecting a defect from the defect image by using the reference image; and
    detecting a defect from the defect image in the determined defect detection processing mode.

12. The defect observation method according to claim 11, wherein the defect detection processing mode includes a defect detection mode using cell comparison in which a defect is detected by comparing repeated patterns in the defect image with each other, and a defect detection mode using die comparison in which a defect is detected by comparing the defect image with the reference image.

13. The defect observation method according to claim 12, wherein a result detected in the defect detection mode using cell comparison is combined with a result detected in the defect detection mode using die comparison, and thus a final defect detection result is fixed.

14. The defect observation method according to claim 12, wherein a difference between a synthesized image which is synthesized on the basis of the repeated patterns in the defect image and the reference image is determined as a noise component in the defect detection mode using cell comparison.

15. The defect observation method according to claim 11, wherein an image of a position detected by the defect detection processing portion is acquired again without moving the stage after the defect image is acquired.

16. The defect observation method according to claim 11, wherein parameters used for a process of detecting the defect can be set to correspond to the determined defect detection mode.

17. The defect observation method according to claim 11, wherein the reference image is acquired at positions where the coordinates of the defect candidates are projected onto a predetermined die which is designated in advance.

18. The defect observation method according to claim 11, wherein a defect detection processing mode is determined according to the presence or absence of a pre-registered pattern in the reference image.

19. The defect observation method according to claim 18, wherein, in a case where the registered pattern is present, a position of the detected defect is not imaged again.

20. The defect observation method according to claim 18, wherein, in a case where the registered pattern is present, an image of a partial region is cut out of the defect image, and an image having a magnification higher than a magnification of the defect image is generated by performing a digital zoom process on the cutout image.

* * * * *